United States Patent [19]

Abood et al.

[11] Patent Number: 5,811,398

[45] Date of Patent: Sep. 22, 1998

[54] PLATELET AGGREGATION INHIBITORS CONTAINING C-TERMINAL AMINERGIC SIDE CHAIN AMINO ACID RESIDUES

[75] Inventors: Norman Anthony Abood, Grove, Ill.; Philippe Roger Bovy, Los Altos, Calif.; Daniel Lee Flynn, Mundelein, Ill.; Joseph Gerace Rico; Thomas Edward Rogers, both of Ballwin, Mich.

[73] Assignee: G. D. Searle & Co., Chicago, Ill.

[21] Appl. No.: 419,793

[22] Filed: Apr. 11, 1995

[51] Int. Cl.$^6$ ....................................... C07K 5/06
[52] U.S. Cl. .............................. 514/19; 514/18; 562/562; 562/571; 530/331
[58] Field of Search ................... 514/18, 19; 562/571, 562/562; 530/331

[56] References Cited

U.S. PATENT DOCUMENTS

| | | | |
|---|---|---|---|
| 5,039,805 | 8/1991 | Alig et al. | 546/224 |
| 5,220,050 | 6/1993 | Bovy | 514/357 |
| 5,256,812 | 10/1993 | Alig et al. | 560/35 |
| 5,273,982 | 12/1993 | Alig et al. | 514/315 |
| 5,430,024 | 7/1995 | Alig | 514/18 |
| 5,561,112 | 10/1996 | Kottivsch | 514/19 |
| 5,663,297 | 9/1997 | Alig | 530/331 |

FOREIGN PATENT DOCUMENTS

| | | |
|---|---|---|
| 0 445 796 a2 | 9/1991 | European Pat. Off. . |
| WO 92/15607 | 9/1992 | WIPO . |

*Primary Examiner*—Cecilia J. Tsang
*Assistant Examiner*—David Lukton
*Attorney, Agent, or Firm*—Cynthia S. Kovacevic

[57] ABSTRACT

This invention relates to compounds having the following formula

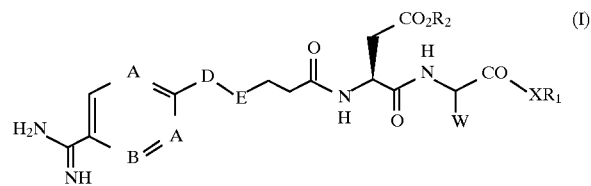

or pharmaceutically acceptable salt thereof which are useful in the inhibition of platelet aggregation, to pharmaceutical compositions containing such compounds, and to a method of inhibiting platelet aggregation in mammals by administering such compounds and compositions.

13 Claims, No Drawings

PLATELET AGGREGATION INHIBITORS CONTAINING C-TERMINAL AMINERGIC SIDE CHAIN AMINO ACID RESIDUES

FIELD OF THE INVENTION

The present invention relates to pharmaceutical agents (compounds) which inhibit platelet aggregation in mammals.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gp IIb/IIIa; this is an important feature of the platelet function. Inhibitors of this interaction are useful in modulating platelet thrombus formation.

It is also known that another large glycoprotein named fibronectin, possesses cell-attachment properties. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., J. Biol. Chem. 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in European Patent Applications 275,748 and 298,820.

European Patent Application 445,796 discloses acetic acid derivatives which have inhibitory action on the bonding of adhesive proteins to blood platelets as well as on blood platelet aggregation and cell-cell adhesion.

U.S. Pat. No. 5,273,982 discloses acetic acid derivatives useful for inhibiting the binding of adhesive proteins to blood platelets and for inhibiting platelet aggregation.

European Patent Application 372,486 discloses N-acyl beta amino acid derivatives and their salts. Said compounds are useful for inhibiting platelet aggregation in the treatment of thrombosis, stroke, myocardial infarction, inflammation and arteriosclerosis, and for inhibiting metastasis.

European Patent Application 381,033 discloses amidino or guanidinoaryl substituted alkanoic acid derivatives useful for the treatment of thrombosis, apoplexy, cardiac infarction, inflammation, arteriosclerosis and tumors.

U.S. Pat. No. 5,220,050 and PCT/US 92/01531 describe phenylamidine containing peptide mimetics which are useful as platelet aggregation inhibitors.

SUMMARY OF THE INVENTION

The present invention relates to a class of compounds represented by the formula:

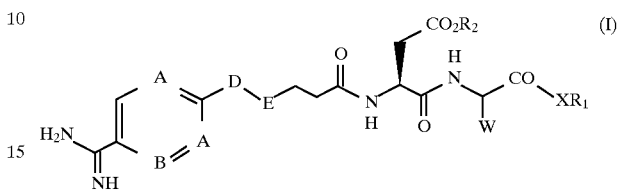

or a pharmaceutically acceptable salt thereof, wherein

A is —CH— or —N—, and B is —CH— or —N—, with the proviso that when A is —N—, B is —CH—, and when B is —N—, then A is —CH—; —D—E— is —CH$_2$—CH$_2$— or

with the proviso that when A is —N— then —D—E— is —CH$_2$—CH$_2$— and when B is —N— then —D—E— is

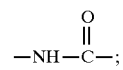

R$_1$ and R$_2$ are independently selected from the group consisting of H, lower alkyl, and optionally substituted aralkyl;

X is selected from the group consisting of —O— and —NH—;

W is selected from the group consisting of

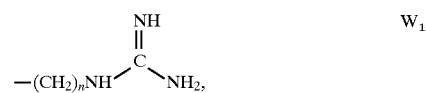 W$_1$

 W$_2$

 W$_3$

 W$_4$

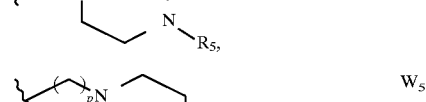 W$_5$

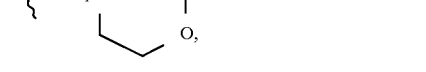 W$_6$ $R_5$ is selected from the group consisting of H, lower alkyl, optionally substituted aralkyl, alkoxycarbonyl, acyl and sulfonyl;

$R_6$ is selected from the group consisting of H, alkyl and optionally substituted aralkyl;

m is an integer selected from the group consisting of 3, 4 and 5;

n is an integer selected from the group consisting of 2 and 3;

is an integer selected from the group consisting of 1, 2 and 3;

r is an integer selected from the group consisting of 1, 2 and 3; and q is an integer selected from the group consisting of 0 and 1.

It is another object of the invention to provide pharmaceutical compositions comprising compounds of the formula I. Such compounds and compositions have usefulness as modulators and/or inhibitors of platelet aggregation. The invention also relates to a method of therapeutically inhibiting or modulating platelet aggregation in a mammal in need of such treatment.

DETAILED DESCRIPTION OF THE INVENTION

The present invention relates to a class of compounds represented by the formula I, described above.

A preferred embodiment of the present invention is compounds wherein W is $W_2$.

Exemplifying this embodiment is the following compound:

N-[4-[[4-(aminoiminomethyl)phenyl]amino-1,4-dioxobutyl]-L-aspartyl-L-lysine bistrifluoroacetate.

As used herein, the term "lower alkyl" refers to a straight chain or branched chain hydrocarbon radical having from 1 to 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the term "aralkyl" refers to a lower alkyl as defined above substituted by an aryl group, wherein the aryl group is an aromatic ring system composed of one or more aromatic or heteroaromatic rings such as phenyl, pyridyl, naphthyl, pyrimidinyl, biphenyl and the like. "Optionally substituted aralkyl" refers to such a radical substituted by groups such as alkyl, alkoxy, hydroxy, halo, amino, nitro, cyano, carboxyl and the like.

As used herein the term "acyl" refers to a radical of the formula $$R_{10}-\overset{\overset{\displaystyle O}{\|}}{C}-$$

wherein $R_{10}$ is lower alkyl, aralkyl or aryl as defined above.

As used herein the term "sulfonyl" refers to a radical of the formula $$-\overset{\overset{\displaystyle O}{\|}}{\underset{\underset{\displaystyle O}{\|}}{S}}-R_{11}$$

wherein $R_{11}$ is an alkyl or aryl group as defined above.

As used herein the term "alkoxycarbonyl" refers to a radical of the formula $$R_{12}-O-\overset{\overset{\displaystyle O}{\|}}{C}-$$

wherein $R_{12}$ is alkyl or aralkyl as defined above.

The compounds as shown in formula I can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of the pharmacologically acceptable salts may be prepared by conventional means. (See Berge et al., *J Pharm. Sci.,* 66(1), 1–19 (1977) for additional examples of pharmaceutically acceptable salts.)

This invention also relates to a method of inhibiting platelet aggregation and more specifically, a method of treatment involving the administration of compounds of Formula I to achieve such inhibition. compounds of the present invention bind to the group IIb/IIIa receptor disrupting the platelet/fibrinogen interaction necessary for thrombus formation. The compounds modulate cell adhesion by competing with RGD containing ligands and by binding to RGD-directed receptors on cell surfaces.

For the inhibition of platelet aggregation, compounds of the present invention may be administered orally, parenterally, or by inhalation spray, rectally, or topically in dosage unit formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus the dosage regimen may vary widely. Dosage levels of the order from about 0.01 mg to about 150 mg per kilogram of body weight per day are useful in the treatment of the above-indicated conditions.

For oral administration, the pharmaceutical composition may be in the form of, for example, a tablet, capsule, suspension or liquid. The pharmaceutical composition is preferably made in the form of a dosage unit containing a particular amount of the active ingredient. These may contain, for example, an amount of active ingredient from about 1 to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

General synthetic sequences useful for preparing the compounds of the invention are described and outlined in the following Schemes. Scheme A, B, C-1, C-2, C-3, C-4, C-5, C-6, C-7, D-1, D-2 and 1-A are 1) general synthetic methods useful for preparing nonproteinaceous aminergic amino acids which form the W side chains of the compounds of the present invention, 2) synthetic methods useful for preparing intermediate alcohols and aldehydes for synthesis of the aminergic amino acids, 3) synthetic methods for preparation of pyrimidinyl and pyridinyl side chains and a 4) general synthesis of compounds of the formula I.

Scheme A illustrates the preparation of intermediate nonproteinaceous amino acid esters or amides 5 using as the key reaction a reductive amination between aldehydes 2 and secondary amines or amides 3. Thus ozonolysis of an N-protected amino acid ester 1 of vinyl glycine (p-1=0), allylglycine (p-1=1), or 4-butenylglycine (p-1=2) affords the intermediate aldehydes 2 after a reductive work-up (dimethylsulfide). In compound 1, $R_8$ is selected from benzyloxycarbonyl (CBZ), t-butoxycarbonyl (BOC), or allyloxycarbonyl (Alloc). Compound 2 subsequently undergoes reductive amination with secondary amine 3, taken from $NR_5(R_6)$ wherein $R_5$ and $R_6$ are restricted to alkyl or optionally substituted aralkyl, pyrrolidine, piperidine, mono-substituted piperazines, or morpholine, to give N-protected amino acid esters 4. Reductive amination is effected using sodium cyanoborohydride, borane/pyridine complex, or sodium triacetoxy borohydride. Alternatively, reductive amination between 2 ($R_8$=BOC) and amine 3 is effected with hydrogen atmosphere/platinum catalysis. Removal of the $R_8$ protecting group under standard conditions (acid treatment for BOC; hydrogenolysis for CBZ or Alloc, or Pd(0)/acetic acid for Alloc) affords the desired amino acid derivatives 5 possessing $W_2$, $W_3$, $W_4$ and $W_5$ containing side-chains.

SCHEME A

PREPARATION OF NONPROTEINACEOUS AMINO ACIDS CONTAINING $W_2$, $W_3$, $W_4$, AND $W_5$ SIDE CHAINS

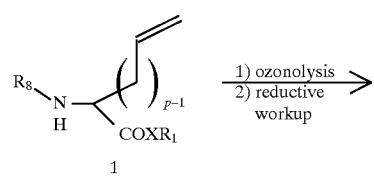

1

SCHEME A -continued

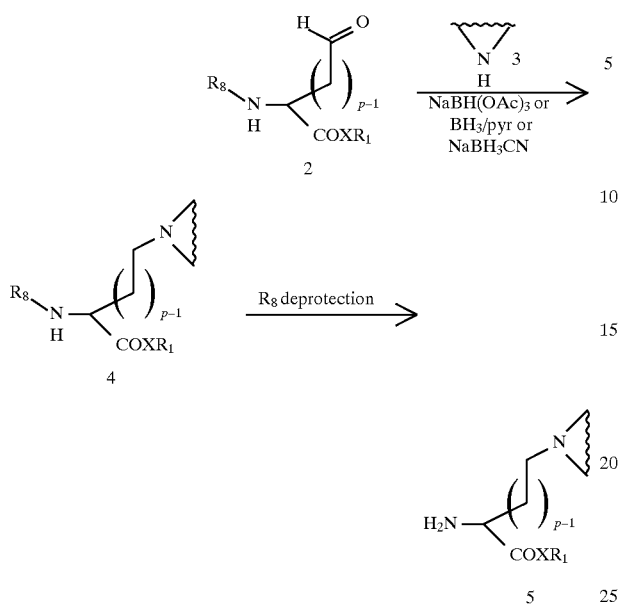

SCHEME B

PREPARATION OF NONPROTEINACEOUS AMINERGIC AMINO ACIDS CONTAINING $W_6$ TO $W_{11}$ AND $W_{13}$ SIDE CHAINS

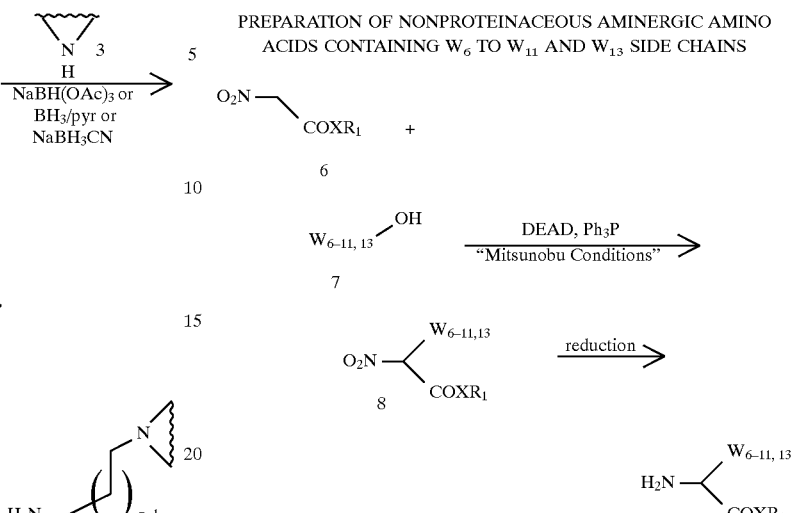

Scheme B illustrates the preparation of intermediate nonproteinaceous amino acid esters using as the key reaction a Mitsunobu reaction between alkyl nitroacetate 6 and a primary alcohol 7. Thus reaction of ethyl nitroacetate (Aldrich Chemical Company) with alcohol 7 in the presence of diethyl azodicarboxylate (DEAD) and triphenylphosphine affords intermediate nitro compound 8, which is then reduced under hydrogen atmosphere using palladium or platinum catalysis to afford the desired amino acid ester 9 possessing $W_6$, $W_7$, $W_8$, $W_9$, $W_{10}$, $W_{11}$, and $W_{13}$ containing side-chains.

$W_1$, $W_2$, and $W_{12}$ containing amino acids are widely known and utilized.

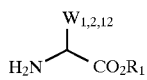

For $W_1$, the natural amino acid arginine corresponds to n=3. For $W_2$, the natural amino acid lysine corresponds to m=4 and $R_5$, $R_6$=H; ornithine corresponds to m=3 and $R_5$, $R_6$=H. $W_{12}$ is widely known, and its synthesis is described by G. E. Stokker et al, *J. Org. Chem.* (1993) 58, 5015.

Scheme C-1 illustrates the preparation of the requisite amino alcohols 7a–c containing a 3-substituted pyrrolidine corresponding to $W_6$. Treatment of commercially available 3-pyrrolidinemethanol 12 (Aldrich Chemical Co.) with an aldehyde or ketone under conditions of reductive amination, or alternatively with an alkylhaloformate, alkyl pyrocarbonate, acid chloride, anhydride, or sulfonyl chloride in the presence of base, preferably triethylamine or di-isopropylethylamine, affords 13 wherein $R_5$ is alkyl, aralkyl, acyl, alkoxycarbonyl, or sulfonyl. Oxidation of intermediate 13 using standard methodology known in the art, preferably Swern oxidation conditions (DMSO, oxalyl chloride, triethylamine) affords ketone 14. Wittig olefination of ketone 14 with methoxymethyltriphenyl-phosphorane affords the enol ether 15, which is hydrolyzed to the aldehyde 10a by treatment with aqueous HCl in the presence of an etheral co-solvent or acetic acid. Two iterations of the Wittig olefination and hydrolysis sequence as described above affords the homologated aldehydes 10b–c. Reduction of 10a–c with standard metal hydride reducing agents, preferably sodium borohydride ($NaBH_4$) in an alcoholic solvent, affords 3-hydroxymethyl-pyrrolidines 7a–c.

SCHEME C-1:

PREPARATION OF INTERMEDIATE ALCOHOLS AND ALDEHYDES FOR SYNTHESIS OF $W_6$ CONTAINING AMINO ACID ESTERS

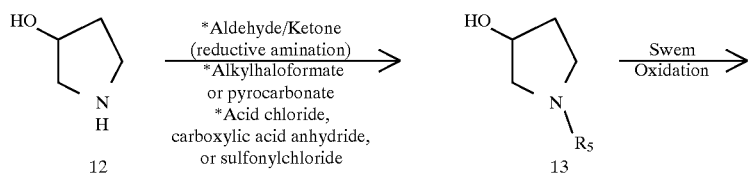

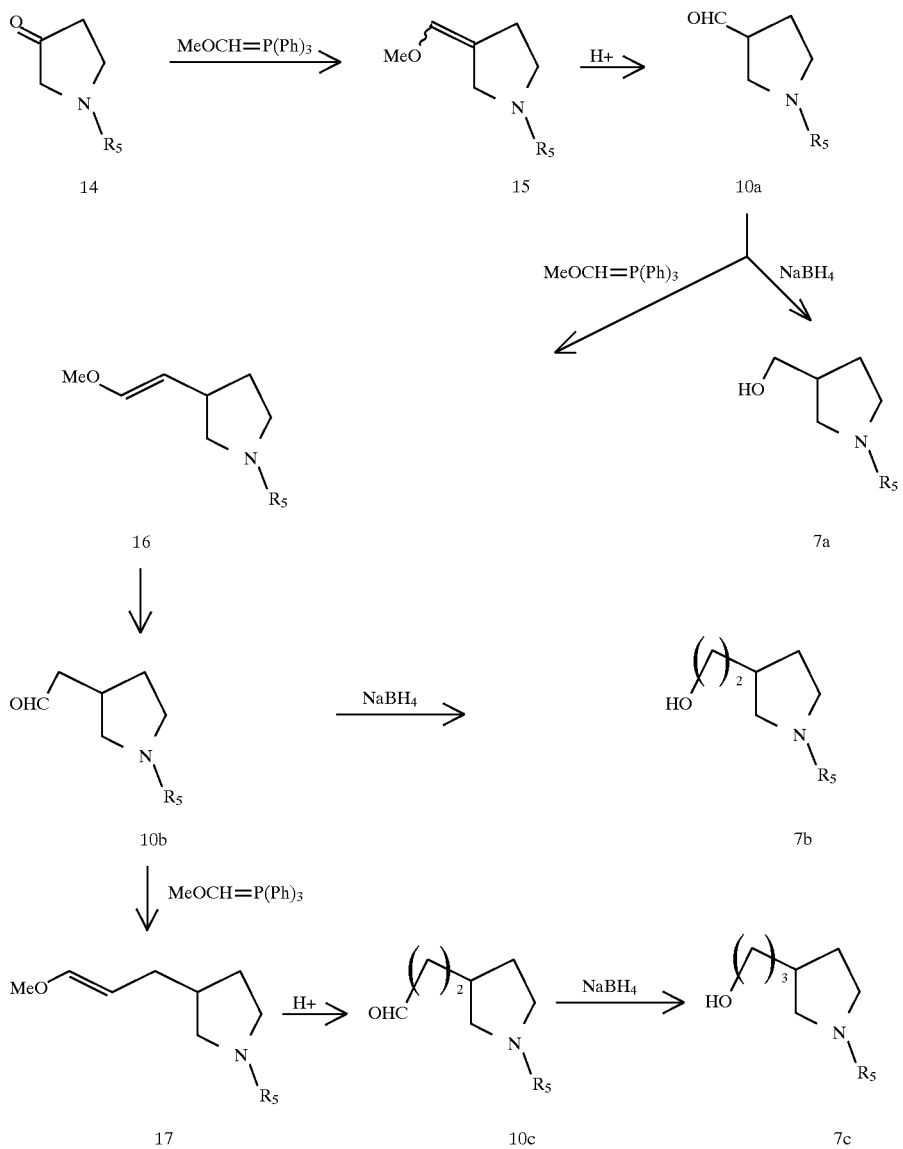

Scheme C-2 illustrates the preparation of 2-hydroxyalkylpyrrolidines. Application of the above-mentioned sequence of reductive amination (alternatively acylation, sulfonylation, carbamoylation) starting from commercially available 2-hydroxymethylpyrrolidine 18 (Aldrich Chemical Company) gives 7d. Subsequent oxidation of 7d affords aldehyde 10d. Iterative Wittig enol ether formation and hydrolysis sequences affords aldehydes 10e–f. Reduction of 10e–f with sodium borohydride affords 2-hydroxyalkylpyrrolidines 7e–f.

SCHEME C-2:

PREPARATION OF INTERMEDIATE ALCOHOLS AND ALDEHYDES FOR SYNTHESIS OF $W_7$ CONTAINING AMINO ACID ESTERS

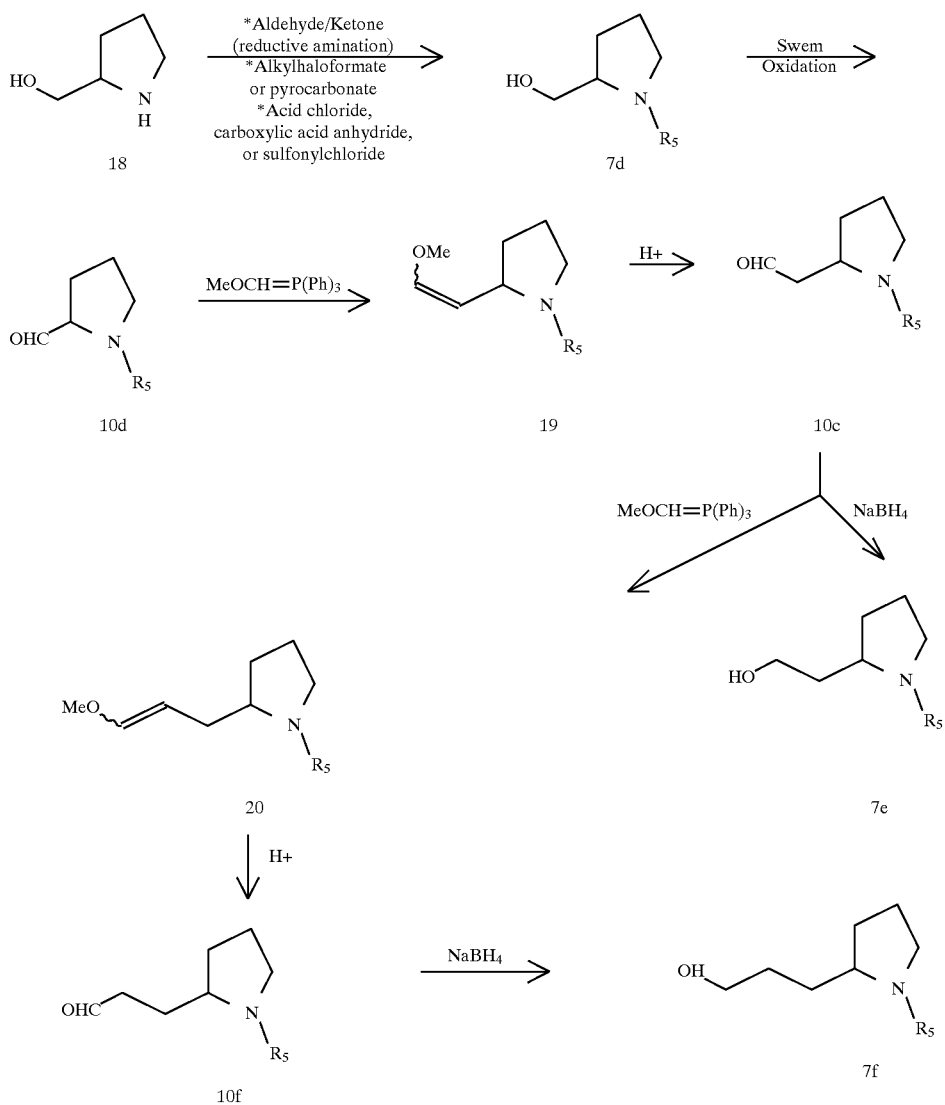

Scheme C-3 illustrates the preparation of 3-hydroxyalkyl substituted piperidines corresponding to $W_8$, starting from reduction of commercially available ethyl nipecotate 21 (Aldrich Chemical Company). Reduction of 21 with sodium borohydride affords the alcohol 22, which is converted to its N-substituted analogs 7g by application of the above-mentioned reductive amination procedure or alternative acylation, sulfonylation, carbamoylation. Oxidation of 7g affords aldehyde 10g, and iterative Wittig enol ether formation and hydrolysis sequences afford aldehydes 10h–i. Reduction of 10h–i with sodium borohydride affords 3-hydroxyalkylpiperidines 7h–i.

SCHEME C-3:

PREPARATION OF INTERMEDIATE ALCOHOLS AND
ALDEHYDES FOR SYNTHESIS OF $W_8$ CONTAINING
AMINO ACID ESTERS

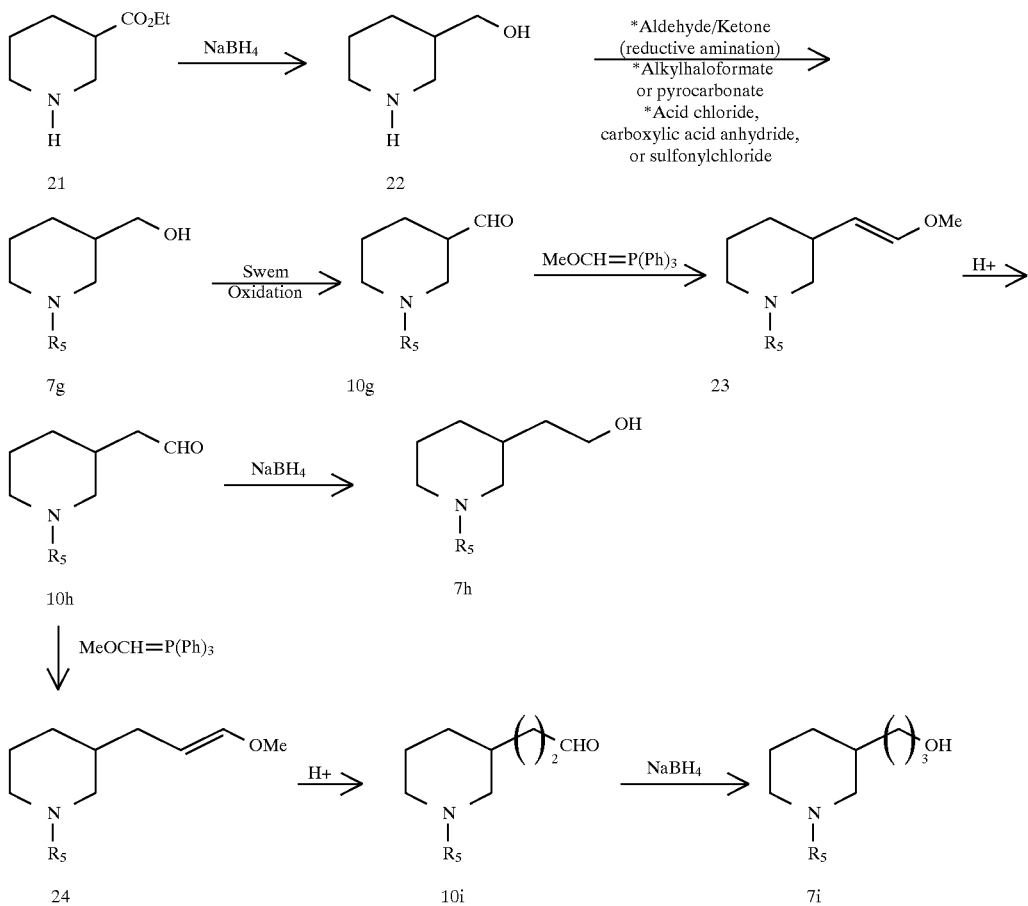

Scheme C-4 illustrates the preparation of 4-hydroxyalkylpiperidines starting from commercially available 1,4-dioxa-8-azaspiro[4.5]decane 25 (Aldrich Chemical Company). Reductive amination or alternative acylation, sulfonylation, carbamoylation affords 26, which gives the ketone 27 upon exposure to acid hydrolysis of the ethylene ketal protecting group. Three iterations of the above-mentioned Wittig olefination and hydrolysis sequence affords aldehydes 10j–l. Reduction of 10j–l with sodium borohydride affords the 4-hydroxyalkylpiperidines 7j–l.

SCHEME C-4: PREPARATION OF INTERMEDIATE ALCOHOLS AND ALDEHYDES FOR SYNTHESIS OF $W_9$ CONTAINING AMINO ACID ESTERS

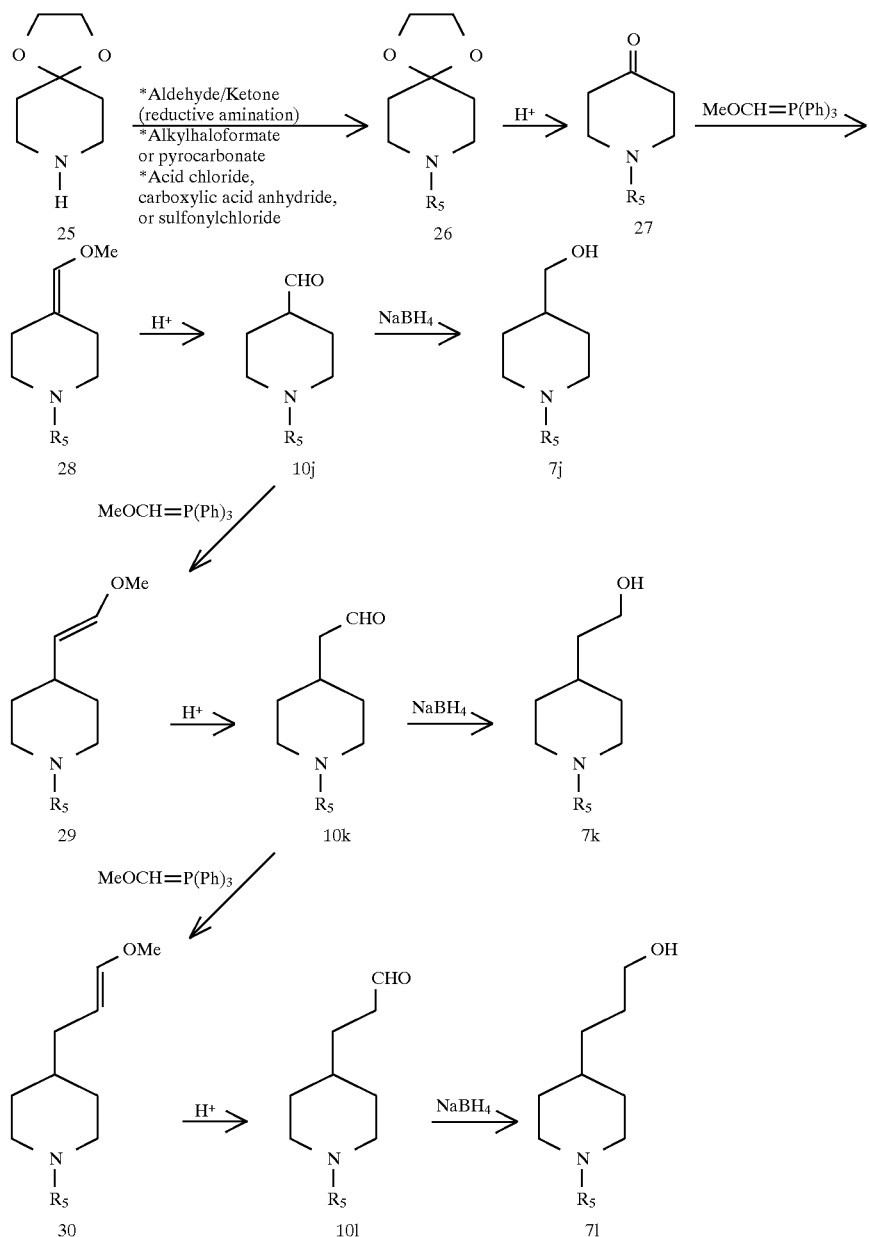

Scheme C-5 illustrates the preparation of 4-hydroxyalkylcyclohexylamines 7m–p starting from commercially available 1,4-cyclohexanedione mono-ethylene ketal 31 (Aldrich Chemical Company). Oximation of 31 with hydroxylamine HCl in the presence of base (sodium acetate or pyridine) affords the oxime 31A, which is then reduced with lithium aluminum hydride in an etheral solvent to afford the primary amine 32 ($R_5$, $R_6$=hydrogen). Treatment of 32 ($R_5$, $R_6$=hydrogen) with an aldehyde or ketone under conditions of reductive amination as described above affords 32 wherein $R_5$ is hydrogen and $R_6$ is alkyl, or optionally substituted aralkyl. Alternatively, treatment of 32 wherein $R_5$, is H and $R_6$ is H, alkyl, or aralkyl with an alkylhaloformate, alkyl pyrocarbonate, acid chloride, anhydride, or sulfonyl chloride in the presence of base, preferably triethylamine or di-isopropylethylamine, affords intermediates 32 wherein $R_5$ is alkoxycarbonyl, acyl, or sulfonyl and $R_6$ is H, alkyl, or aralkyl. Alternatively, reaction of ketone 31 with a primary or secondary amine under conditions of reductive amination affords 32 wherein $R_5$ and $R_6$ are selected from hydrogen, alkyl, or aralkyl (excepting that $R_5$ and $R_6$ are not both hydrogen). Acidic hydrolysis of the ketal 32 affords the ketone 33, which is subjected to the conditions of Wittig olefination using methoxymethyltriphenyl-phosphorane to give enol ether 34. Acidic hydrolysis of 34 gives the aldehyde 10m, which is converted to the homologated aldehydes 10n–p by iterative Wittig olefination and acidic hydrolysis. The aldehydes 10m–p are reduced to the desired hydroxyalkylcyclohexylamine derivatives 7m–p by reaction with sodium borohydride in an alcoholic solvent.

alkyl or aralkyl. Alternatively, reaction of 38 ($R_6$ is hydrogen and $R_5$ is alkoxycarbonyl, acyl, or sulfonyl) with base (e.g. sodium hydride or lithium di-isopropylamide) in an etheral

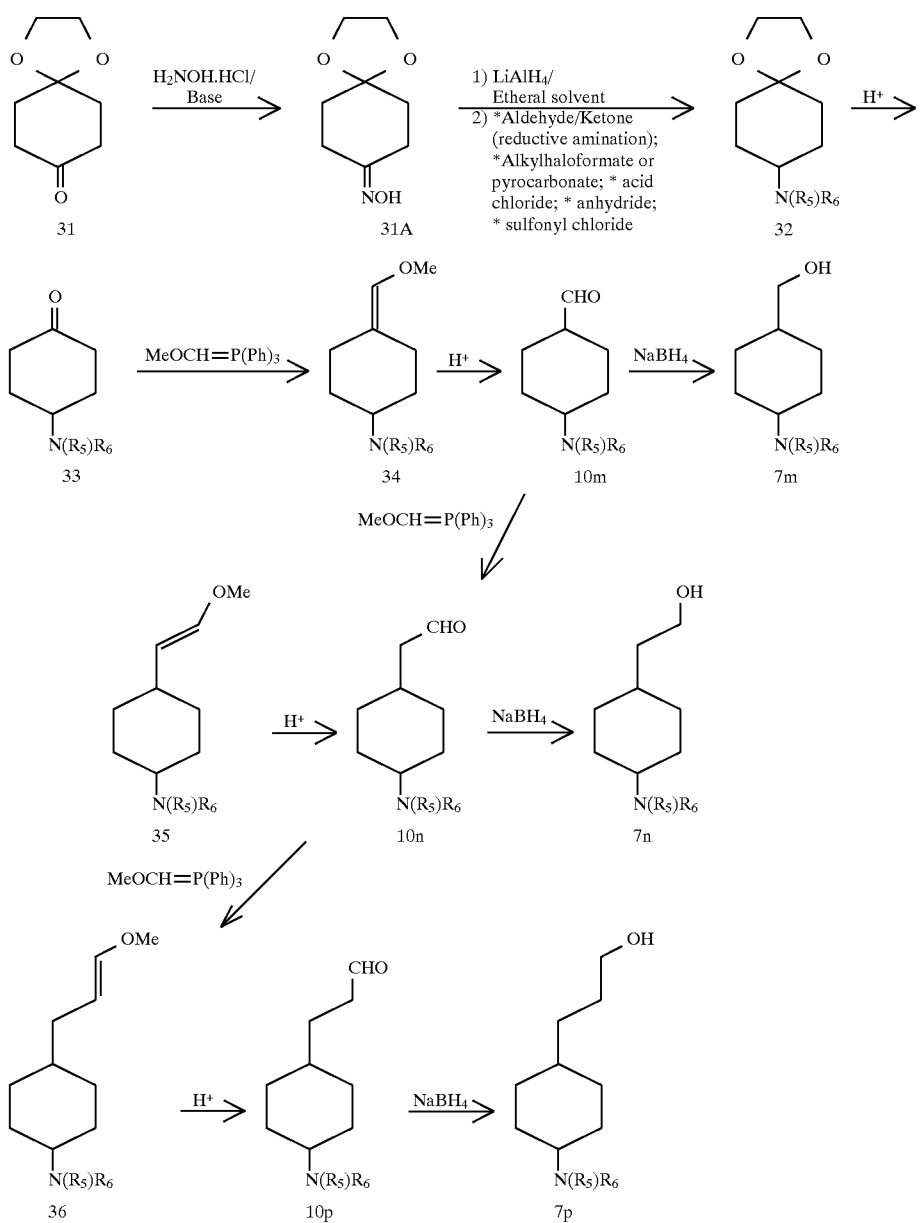

SCHEME C-5: PREPARATION OF INTERMEDIATE ALCOHOLS AND ALDEHYDES FOR SYNTHESIS OF $W_{10}$ CONTAINING AMINO ACID ESTERS

Scheme C-6 illustrates the preparation of 4-hydroxyalkylaniline derivatives starting from commercially available ethyl 4-aminobenzoate 37 (Aldrich Chemical Company). Treatment of 37 with an aldehyde or ketone under conditions of reductive amination affords 38 wherein $R_5$ is H and $R_6$ is alkyl, or aralkyl. Alternatively, treatment of 37 or 38 ($R_5$ is hydrogen and $R_6$ is alkyl or optionally-substituted aralkyl) with an alkylhaloformate, alkyl pyrocarbonate, acid chloride, anhydride, or sulfonyl chloride in the presence of base, preferably triethylamine or di-isopropylethylamine, affords intermediate 38 wherein $R_5$ is alkoxycarbonyl, acyl, or sulfonyl and $R_6$ is hydrogen, solvent or dipolar aprotic solvent (preferably sodium hydride in N,N-dimethylformamide) followed by an alkyl- or aralkyl-halide or sulfonate affords compounds 38 wherein $R_6$ is alkyl or aralkyl and $R_5$ is selected from alkoxycarbonyl, acyl, or sulfonyl. Reduction of the ester group of 38 with di-isobutylaluminum hydride (DiBAlH) affords aldehyde 10q. Wittig olefination of 10q with methylenetriphenylphosphorane affords 39, which is hydroborated with borane or a substituted borane, preferably 9-borabicyclononane (9-BBN), and then oxidized with hydrogen peroxide in the presence of base to give 4-(2-hydroxyethyl)aniline 7r. Alternatively, reaction of 10q with the stabilized ethoxycarbonylmethylenetriphenylphosphorane affords 40, which is reduced with hydrogen and Pd or Pt catalyst to the saturated ester 41. Reduction of aldehyde 10q or ester 41 with sodium borohydride gives 4-hydroxyalkylaniline 7q or 7s, respectively.

starting from readily available tropanones or homotropanones 42. Iterative Wittig olefination and hydrolysis as described above gives the aldehydes 10t–v. Reduction of these aldehydes with sodium borohydride gives the desired hydroxyalkyl(homo)tropanes 7t–v.

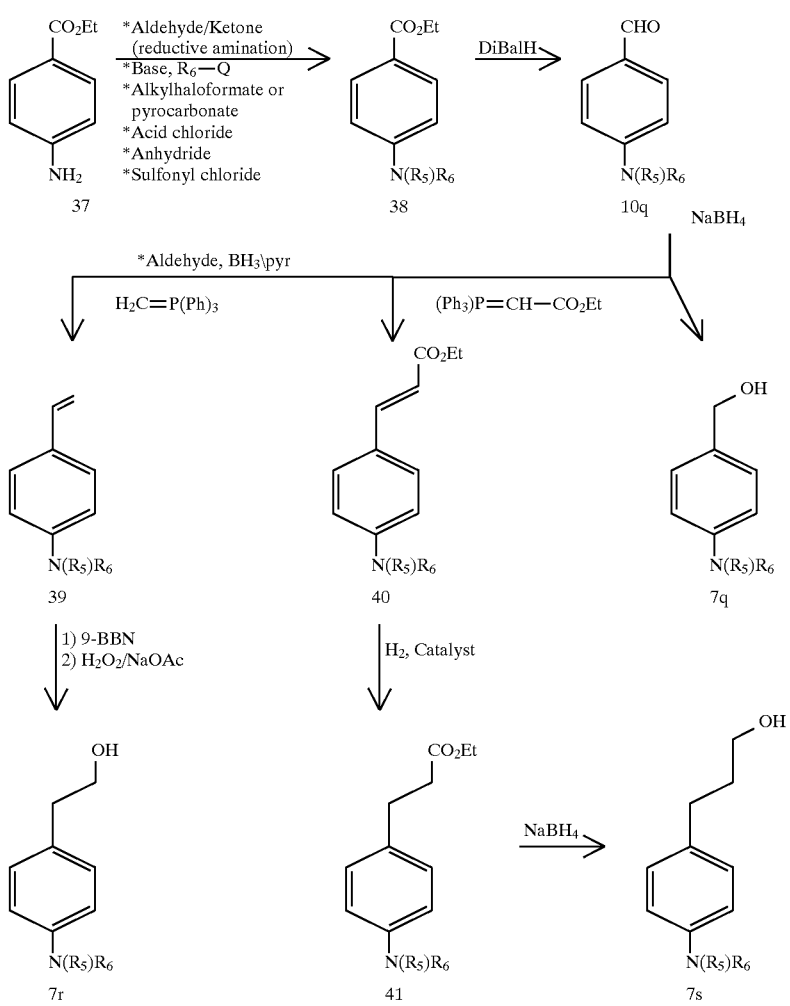

Scheme C-7 illustrates the preparation of hydroxyalkyltropanes (q=0) and hydroxyalkylhomotropanes (q=1) 7t–v

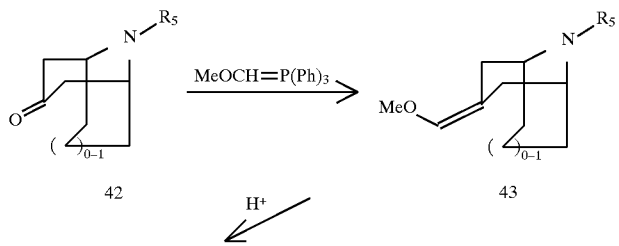

SCHEME C-7: PREPARATION OF INTERMEDIATE ALCOHOLS AND ALDEHYDES FOR SYNTHESIS OF $W_{13}$ CONTAINING AMINO ACID ESTERS —continued

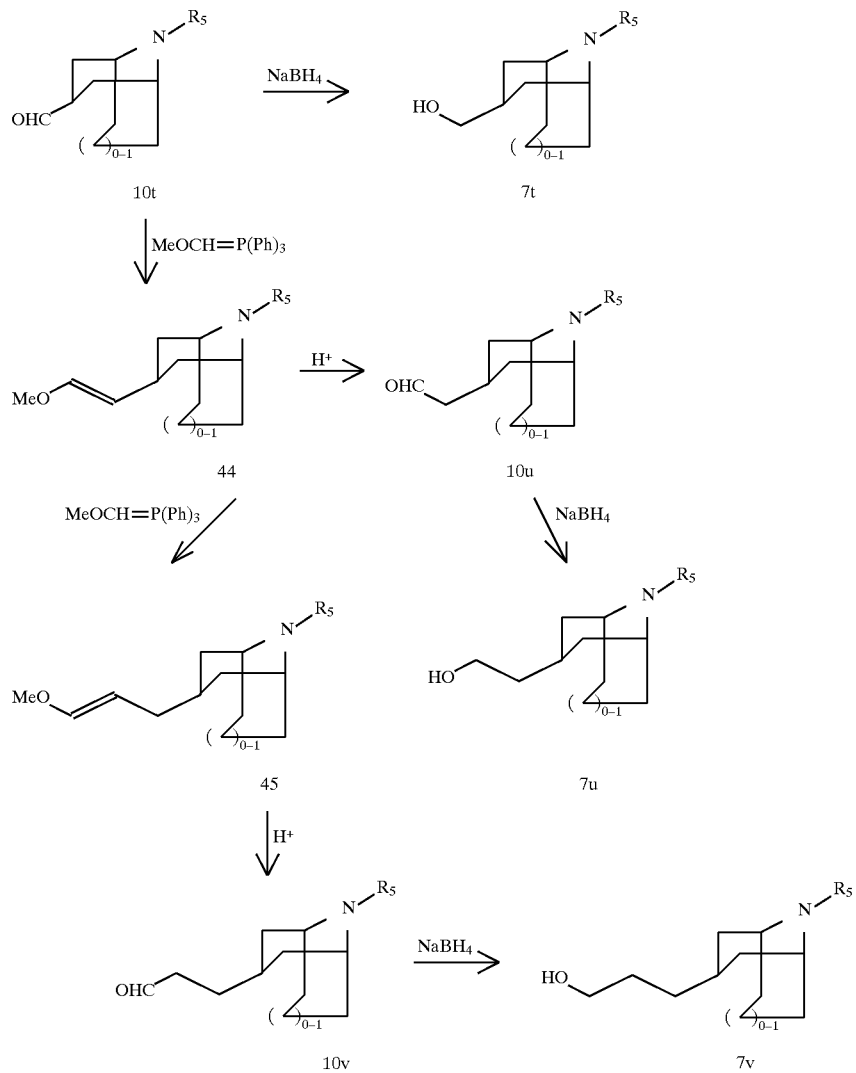

Scheme D-1 illustrates the preparation of 5-(5-amidinylpyrimidin-2-yl)pentanoic acid 53a. Pinner amidination of commercially available nitrile 46 (Pfaltz and Bauer) affords amidine 47, which is condensed with 2-cyano-3-dimethylaminoacrolein 50 (C. Reichart et al, *Angew. Chem. Inter. Ed.*, (1972), 11, 62) under basic conditions, preferably pyridine triethylamine, at temperatures ranging from 20° C. to reflux temperatures to afford the 5-cyanopyrimidine ester 51. Dilute aqueous acid hydrolysis of 51 gives nitrile 52. Ammonolysis in an alcoholic solvent, followed by treatment with HCl, affords 5-(5-amidinylpyrimidin-2-yl)pentanoic acid 53a as the hydrochloride salt.

SCHEME D-1: PREPARATION OF 5-(5-AMIDINYL-PYRIMIDIN-2-YL)PENTANOIC ACID

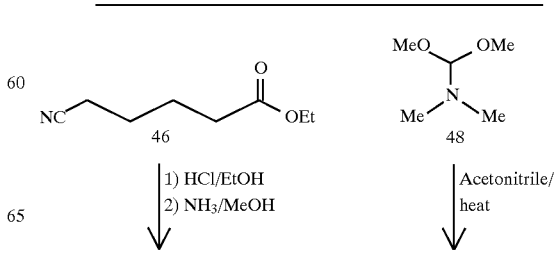

SCHEME D-1: PREPARATION OF 5-(5-AMIDINYL-PYRIMIDIN-2-YL)PENTANOIC ACID

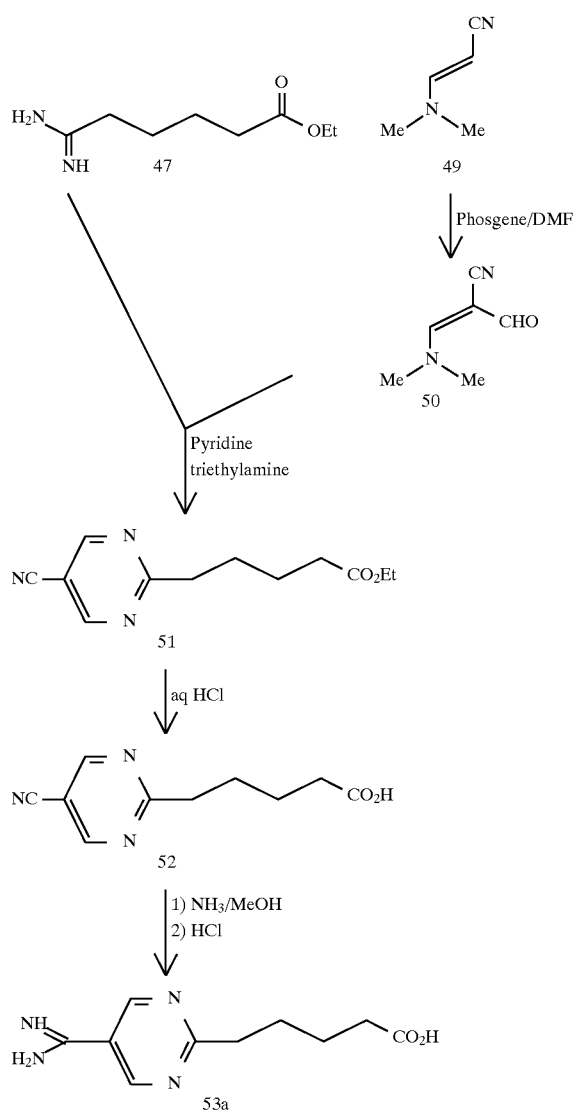

SCHEME D-2: PREPARATION OF 4-(6-AMINOIMINOMETHYL PYRIDIN-3-YL)AMINO-1, 4-DIOXOBUTANOIC ACID HCL 53B

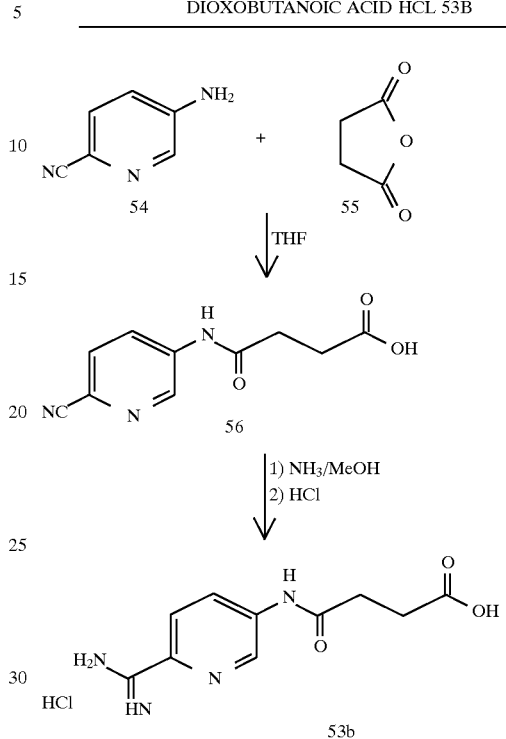

Scheme D-2 illustrates the preparation of 4-(6-aminoiminomethyl pyridin-3-yl)amino-1,4-dioxobutanoic acid HCl 53b. 3-Amino-6-cyano-pyridine 54 was added to succinic anhydride 55 in an etheral solvent, preferably tetrahydrofuran (THF) at ambient temperature, to afford nitrile 56. Treatment of 56 with ammonia saturated in an alcoholic solvent, preferably methanol at 80° C. for 24 hours gave 53b, isolated as the hydrochloride salt after treatment of the residue with HCl/dioxane.

Scheme 1A illustrates the general route utilized to obtain compounds of formula I. Activation of N-protected aspartic acid gamma-t-butyl ester 57 with iso-butylchloroformate (or other activating method, not limited to but including disuccinylcarbonate, 2-chloro-1-methyl-pryridinium iodide, carbonyldiimidazole, or 1-(3-dimethylaminopropyl)-3-ethylcarbodiimide hydrochloride) in the presence of a tertiary amine base (N-methylmorpholine, N-methylpiperazine, triethylamine, di-isopropylethylamine) and subsequent reaction with amino acid ester 58 gives the desired amide condensation product 59. Removal of the nitrogen $R_8$ protecting group (hydrogenolysis [CBZ], acid treatment [BOC], secondary amine base [Fmoc], or Pd(0)/acetic acid [Alloc]) affords the amino-terminal dipeptide 60. Condensastion of 60 with 53a–d, activated as described above for 57, gives 61. Acidic deprotection of the aspartyl side chain t-butyl ester and optional removal of $R_1$ and $W_{1-13}$ containing protecting groups afford the desired compounds of formula I.

SCHEME 1A: SYNTHESIS OF COMPOUND OF GENERAL FORMULA I

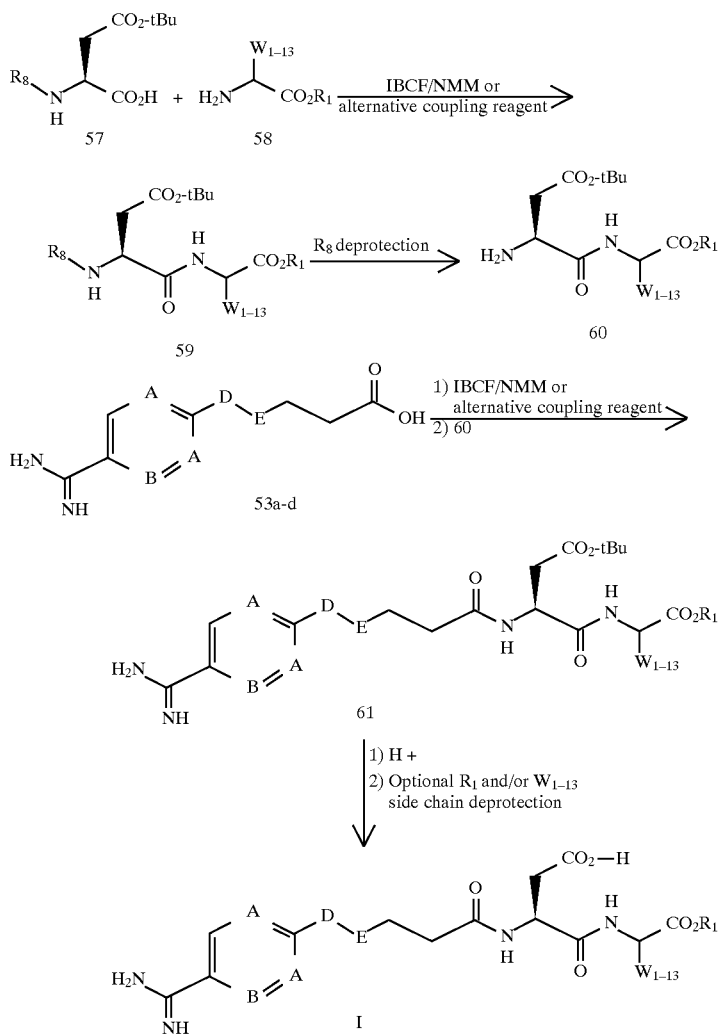

The synthesis of Example 1 is illustrated in Scheme 1B. Commercially available 57a and 58a were coupled, utilizing the standard iso-butylchloroformate/N-methylmorpholine procedure, to afford dipeptide 59a. Hydrogenolysis of the CBZ protecting group (hydrogen atmosphere, palladium/C catalysis) gave the N-terminal amino dipeptide 60a. Coupling of 60a with acid 53c (J. G. Rico et al, *J. Org. Chem.* (1993) 58, 7948) using iso-butylchloroformate/N-methylmorpholine gave 61a, which afforded Example 1 after treatment with trifluoroacetic acid.

SCHEME 1B: SYNTHESIS OF EXAMPLE 1

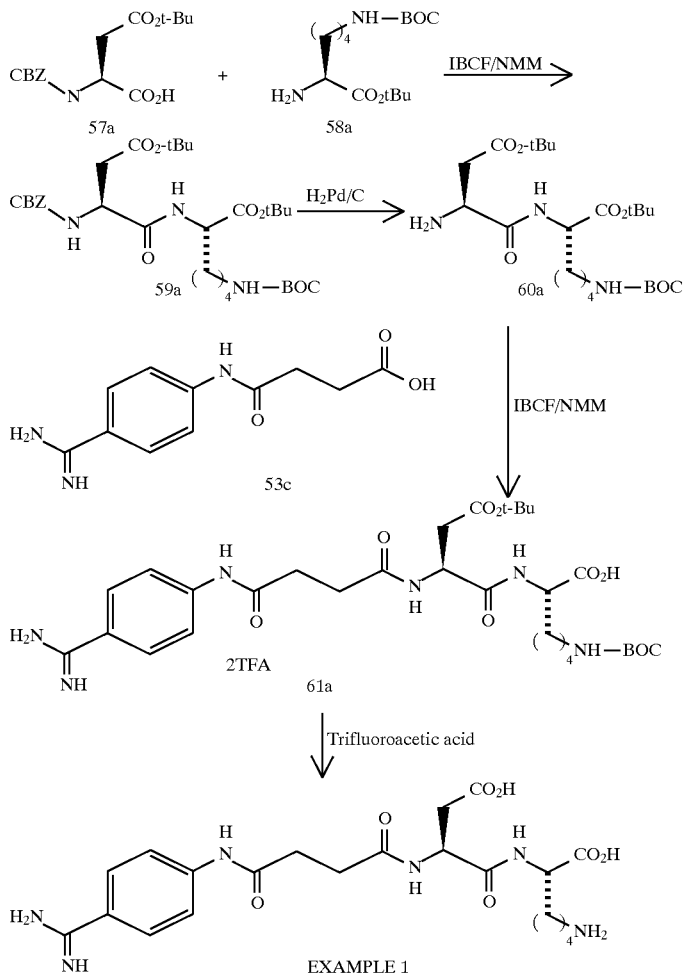

The following example is provided to illustrate the present invention and is not intended to limit the scope thereof. Those skilled in the art will readily understand that known variations of the conditions and processes of the following preparative procedures can be used to prepare the compounds of the present invention.

EXAMPLE 1

N-[4-[[4-(aminoiminomethyl)phenyl]amino]-1,4-dioxobutyl]-L-aspartyl]-L-lysine bistrifluoroacetate

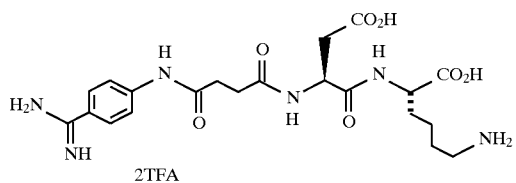

Step A

Preparation of N-Cbz-Asp (Ot-Bu)-Lys (Nε-Boc) Ot-Bu) (3)

To an ice cooled solution of N-Cbz-Asp β-t-butyl ester (1.50 g, 4.46 mmol) and N-methylmorpholine (467 mg, 4.64 mmol) in 45 mL of $CH_2Cl_2$ was added isobutylchloroformate (633 mg, 4.64 mmol). After stirring at $-10°$ C. for 10 minutes, Nε-Boc-Lys t-butyl ester hydrochloride (1.57 g, 4.64 mmol) and N-methylmorpholine (467 mg, 4.64 mmol) were added sequentially. The reaction mixture was allowed to warm to room temperature while stirring for 18 hours. The mixture was diluted with EtOAc and washed successively with water, 10% $NaHSO_4$, 10% $KHCO_3$, and brine. The solvent was dried ($Na_2SO_4$), filtered and evaporated under reduced pressure affording 2.95 g of product.

$^1$H-NMR (200 MHz, $CDCl_3$) δ 1.20–1.92 (m, 8H), 1.43 (s, 18H), 1.46 (s, 9H), 2.63 (m, 1H), 2.97 (m, 1H), 3.07 (br. q, J=7 Hz, 2H), 4.43 (m, 1H), 4.55 (m, 1H), 4.70 (broad, 1H, exchangeable), 5.14 (s, 2H), 5.97 (br. d, J=7 Hz, 1H, exchangeable), 7.00 (br. d, J=7 Hz, 1H, exchangeable), 7.20–7.30 (m, 5H).

Step B

Preparation of $H_2N$-Asp (Ot-Bu)-Lys (Nε-Boc)Ot-Bu (4)

A mixture of the product of Step A (2.77 g, 4.30 mmol) and 4% Pd/C (0.25 g) in 50 mL of MeOH was shaken at 60 psi hydrogen pressure for 8 hours at room temperature. After removal of the catalyst and removal of the solvent under reduced pressure, the residue was taken up in benzene and evaporated. This was repeated 3X to remove residual MeOH and thus obtain 1.92 g of product.

$^1$H-NMR (300 MHz, CDCl$_3$) δ 1.20–1.90 (m, 33H), 2.58 (m, 1H), 2.80 (m, 1H), 3.10 (br. q, J=7 Hz, 2H), 3.68 (m, 1H), 4.45 (m, 1H), 4.72 (broad, 1H, exchangeable), 7.88 (br. d, J=7 Hz, 1H, exchangeable).

Step C

Preparation of N-[4-[[4-(aminoiminomethyl)phenyl]amino]-1,4-dioxobutyl]-L-aspartyl]-L-lysine bistrifluoroacetate (Compound A)

To a stirred mixture of 4-[[4-(aminoiminomethyl)-phenyl]amino]-4-oxobutanoic acid hydrochloride (500 mg, 1.84 mmol) and N-methylmorpholine (220 mg, 2.19 mmol) in 8 mL of DMF was added isobutylchloroformate (290 mg, 0.284 mmol). After stirring at room temperature for 5 minutes, a solution of the product of step B (1.04 g, 2.19 mmol) in 8 mL of DMF was added. After stirring for 18 hours at room temperature, the solvent was removed under reduced pressure. The residue was dissolved in 20 mL of TFA/water 9:1 and stirred at room temperature for 1 hour. After removal of the solvent under reduced pressure, the crude product was purified by RPHPLC (gradient elution 0.05% aq. TFA/acenitrile 95:5 to 60:40 over 30 minutes) using a Delta-Pak C-18 column affording 740 mg of product as the bis TFA salt.

Anal. calc'd. for C$_{21}$H$_{30}$N$_6$O$_7$.2 TFA.1.5 H$_2$O: C, 40.93; H, 4.81:N, 11.46 Found: C, 40.90:H, 4.45:N, 11.61.

$^1$H-NMR (300 MHz, CD$_3$OD) δ 1.40–2.00 (m, 6H), 2.61 (m, 2H), 2.74–2.86 (m, 4H), 2.91 (t, J=7 Hz, 2H), 4.44 (m, 1H), 4.73 (m, 1H), 7.77 (d, J=8 Hz, 2H), 7.92 (d, J=8 Hz, 2H).

The platelet-binding inhibitor activity of the compounds of the present invention can be demonstrated by the assays presented below.

In-Vitro Platelet Aggregation in PRP

Healthy male or female dogs were fasted for 8 hours prior to drawing blood; then 30 ml whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×10$^8$ platelets per ml. 400 μl of the PRP preparation and 50 μl of the compound to be tested or saline were preincubated for 1 minute at 37° C. in a BioData aggregometer (BioData, Horsham, Pa.). 50 μl of adenosine 5'-diphosphate (ADP) (50 μm final concentration) was added to the cuvettes and the aggregation was monitored for 1 minute. All compounds are tested in duplicate. Results are calculated as follows:

Percent of control =

[(maximal OD minus initial OD of compound) divided by (maximal OD minus initial OD of control saline)] ×

100. The % inhibition = 100 − (percent of control).

The assay results for the compound of Example 1 and its median inhibitory concentration (IC$_{50}$) is recorded in Table I.

TABLE I

| Example | Dog PRP IC$_{50}$ |
| --- | --- |
| 1 | 0.18 μM |

What is claimed is:
1. A compound of the formula

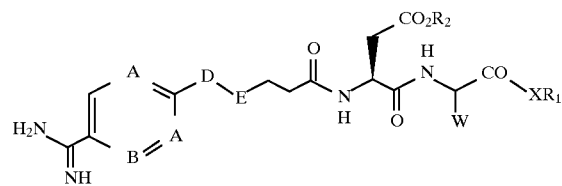

or a pharmaceutically acceptable salt thereof, wherein

A is —CH— or —N—, and B is —CH— or —N—, with the proviso that when A is —N—, B is —CH—, and when B is —N—, then A is —CH—;

—D—E— is —CH$_2$—CH$_2$— or

with the proviso that when A is —N— then —D—E— is —CH$_2$—CH$_2$— and when B is —N— then —D—E— is

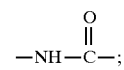

R$_1$ and R$_2$ are independently selected from the group consisting of H, lower alkyl, and aralkyl;

X is selected from the group consisting of —O— and —NH—;

W is selected from the group consisting of

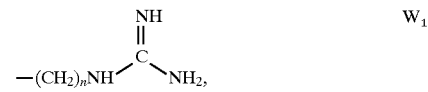 W$_1$

 W$_2$

 W$_3$

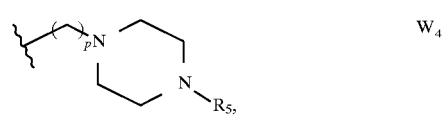 W$_4$ $R_5$ is selected from the group consisting of H, lower alkyl, aralkyl, alkoxycarbonyl, acyl and sulfonyl;

$R_6$ is selected from the group consisting of H, alkyl and aralkyl;

m is an integer selected from the group consisting of 3, 4 and 5;

n is an integer selected from the group consisting of 2 and 3;

p is an integer selected from the group consisting of 1, 2 and 3;

r is an integer selected from the group consisting of 1, 2 and 3; and q is an integer selected from the group consisting of 0 and 1.

2. A compound according to claim 1 wherein W is $-(CH_2)_m N(R_5)R_6$.

3. A compound according to claim 2 which is N-[4-[[4-(aminoiminomethyl)phenyl]amino]-1,4-dioxobutyl]-L-aspartyl]-L-lysine bistrifluoroacetate.

4. A compound according to claim 1 wherein W is $W_1$.

5. A compound according to claim 1 wherein W is selected from the group consisting of $W_3$, $W_4$ and $W_5$.

6. A compound according to claim 1 wherein W is selected from the group consisting of $W_6$, $W_7$, $W_8$, $W_9$, $W_{10}$, $W_{11}$ and $W_{12}$.

7. A compound according to claim 1 wherein W is $W_{13}$.

8. A pharmaceutical composition comprising a therapeutically effective amount of a compound of the formula or a pharmaceutically acceptable salt thereof, wherein A is —CH— or —N—, and B is —CH— or —N—, with the proviso that when A is —N—, B is —CH—, and when B is —N—, then A is —CH—;

—D—E— is —CH$_2$—CH$_2$— or $$-NHC(O)-$$

with the proviso that when A is —N— then —D—E— is —CH$_2$—CH$_2$— and when B is —N— then —D—E— is $$-NH-C(O)-;$$

$R_1$, and $R_2$ are independently selected from the group consisting of H, lower alkyl, and aralkyl;

X is selected from the group consisting of —O— and —NH—;

W is selected from the group consisting of

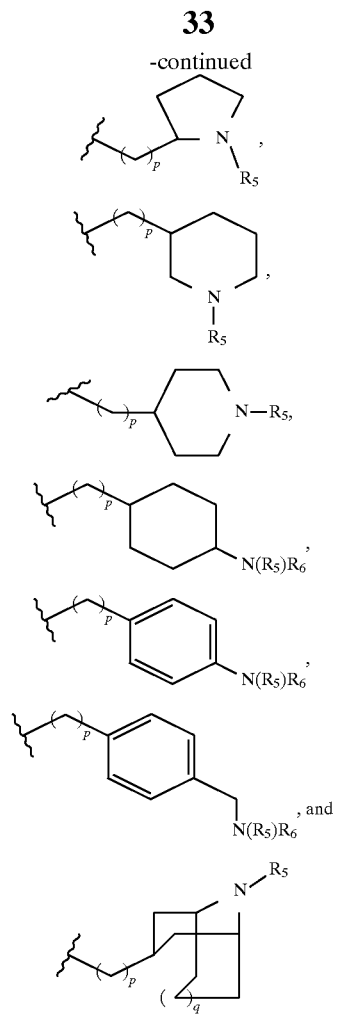

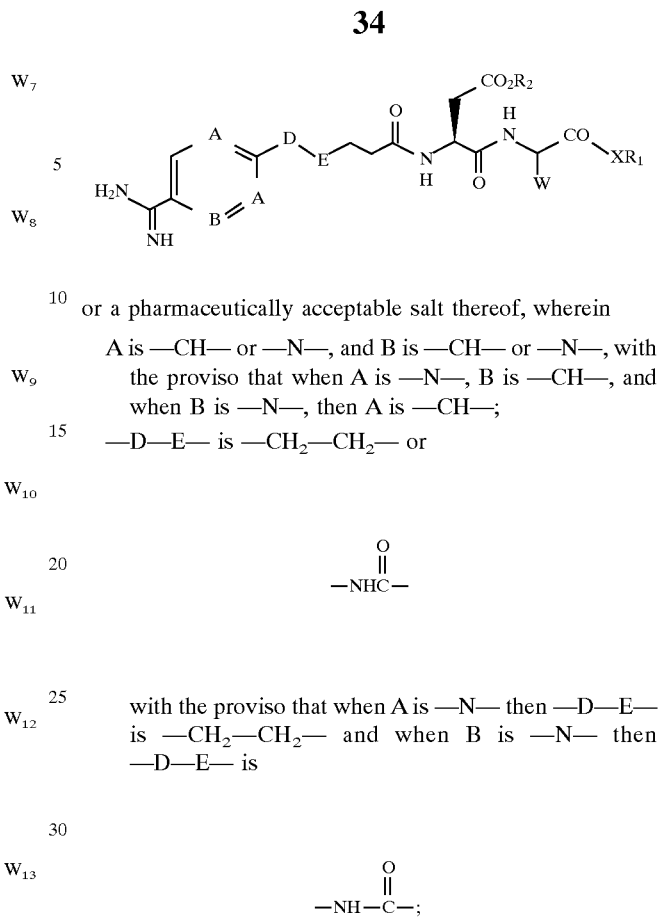

or a pharmaceutically acceptable salt thereof, wherein

A is —CH— or —N—, and B is —CH— or —N—, with the proviso that when A is —N—, B is —CH—, and when B is —N—, then A is —CH—;

—D—E— is —CH$_2$—CH$_2$— or $$-NHC- \atop \overset{O}{\|}$$

with the proviso that when A is —N— then —D—E— is —CH$_2$—CH$_2$— and when B is —N— then —D—E— is $$-NH-\overset{O}{\underset{\|}{C}}-;$$

$R_1$ and $R_2$ are independently selected from the group consisting of H, lower alkyl, and aralkyl;

X is selected from the group consisting of —O— and —NH—;

W is selected from the group consisting of

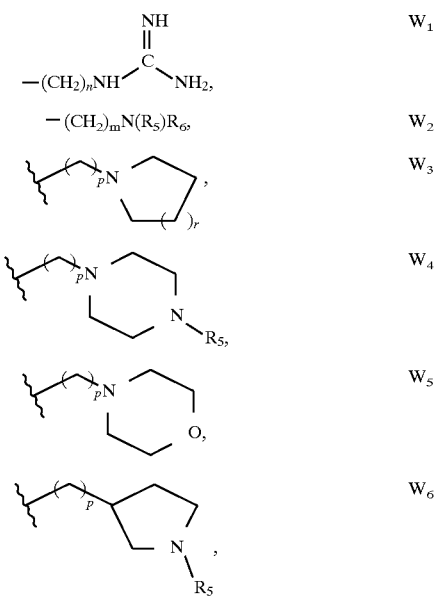

$R_5$ is selected from the group consisting of H, lower alkyl, aralkyl, alkoxycarbonyl, acyl and sulfonyl;

$R_6$ is selected from the group consisting of H, alkyl and aralkyl;

m is an integer selected from the group consisting of 3, 4 and 5;

n is an integer selected from the group consisting of 2 and 3;

p is an integer selected from the group consisting of 1, 2 and 3;

r is an integer selected from the group consisting of 1, 2 and 3;

q is an integer selected from the group consisting of 0 and 1; and a pharmaceutically acceptable carrier.

9. A pharmaceutical composition according to claim 8 wherein W is —(CH$_2$)$_m$NR$_5$R$_6$.

10. A pharmaceutical composition according to claim 9 wherein the compound is N-[4-[[4-(aminoiminomethyl)phenyl]amino]-1,4-dioxobutyl]-L-aspartyl]-L-lysine bistrifluoroacetate.

11. A method of treating a mammal to inhibit platelet aggregation comprising administering a therapeutically effective amount of a compound of the formula

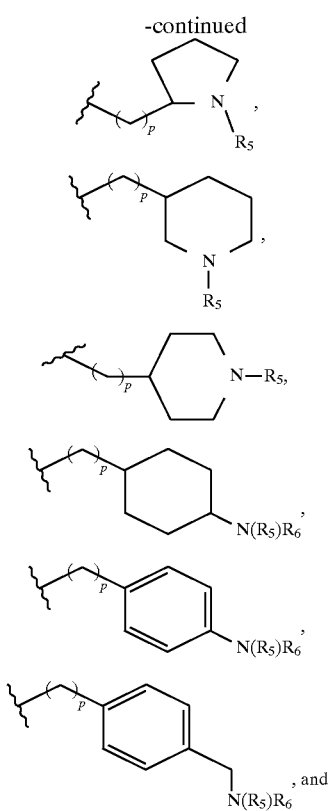

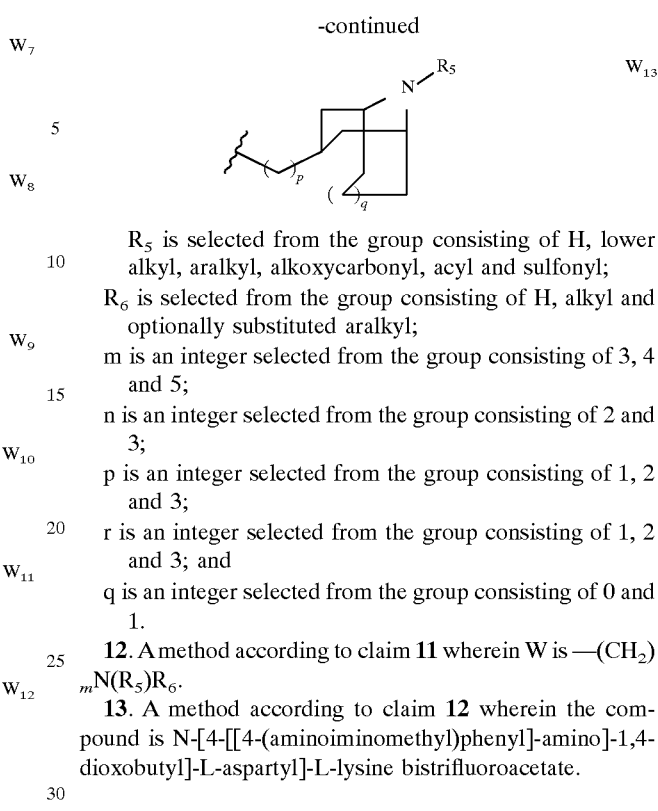

$R_5$ is selected from the group consisting of H, lower alkyl, aralkyl, alkoxycarbonyl, acyl and sulfonyl;

$R_6$ is selected from the group consisting of H, alkyl and optionally substituted aralkyl;

m is an integer selected from the group consisting of 3, 4 and 5;

n is an integer selected from the group consisting of 2 and 3;

p is an integer selected from the group consisting of 1, 2 and 3;

r is an integer selected from the group consisting of 1, 2 and 3; and q is an integer selected from the group consisting of 0 and 1.

12. A method according to claim 11 wherein W is —$(CH_2)_m N(R_5)R_6$.

13. A method according to claim 12 wherein the compound is N-[4-[[4-(aminoiminomethyl)phenyl]-amino]-1,4-dioxobutyl]-L-aspartyl]-L-lysine bistrifluoroacetate.

* * * * *